(12) United States Patent
Tsaur

(10) Patent No.: US 6,960,041 B2
(45) Date of Patent: Nov. 1, 2005

(54) MULTI-FLUID APPLICATOR

(76) Inventor: Garry Tsaur, 19222 Tranbarger St., Rowland Heights, CA (US) 91748

( * ) Notice: Subject to any disclaimer, the term of this patent is extended or adjusted under 35 U.S.C. 154(b) by 0 days.

(21) Appl. No.: 10/705,337

(22) Filed: Nov. 10, 2003

(65) Prior Publication Data

US 2005/0100389 A1    May 12, 2005

(51) Int. Cl.[7] .......................... B43K 5/14; A61M 35/00
(52) U.S. Cl. ..................... 401/133; 401/132; 604/3; 206/222
(58) Field of Search ................... 401/40–43, 132, 401/133, 183–186; 604/1–3; 206/219–222

(56) References Cited

U.S. PATENT DOCUMENTS 2,714,475 A * 8/1955 Roehrich ................ 222/501
3,349,966 A * 10/1967 Schwartzman ............ 222/80
4,875,602 A * 10/1989 Chickering et al. ........ 222/187

* cited by examiner

Primary Examiner—David J. Walczak
(74) Attorney, Agent, or Firm—Joe Nieh

(57) ABSTRACT

A multi-fluid applicator with one or more fluids sealed separately within it with opening device enclosed within the applicator to allow the commingling and releasing of the fluids enclosed within the applicator. The enclosed opening device may be operated by either squeezing or bending the applicator at or near the enclosed opening device. Once the enclosed opening device is opened, the fluids sealed within the elongated sealed container will commingle with each other and be released for application or may be released directly for application. There are no loose parts that may be lost and the fluids are completely sealed within the applicator.

30 Claims, 3 Drawing Sheets

MULTI-FLUID APPLICATOR

BACKGROUND

1. Field of Invention

The present invention relates generally to an applicator with fluids sealed within it. More specifically, the present invention relates to an applicator with one or more fluids sealed separately within it with opening means enclosed within the applicator to allow the commingling and releasing of the fluids enclosed within the applicator.

2. Description of Related Art

Applicators such as cotton swabs are generally used to apply medication, anesthetic, alcohol, and various other liquids. Swab applicator generally comprises of a tubular handle with a formed absorbent tip at one or both ends of the tubular handle. The absorbent tip may be made of cotton or a foam absorbent material. The tip may also be a brush. The tubular handle may be made of wood, paper, or plastic and it may be solid or hollow.

Generally the applicator tip of a dry swab applicator is first placed in contact with the liquid to be applied for the applicator tip to absorb the liquid. Subsequently, the moisturized applicator tip is placed in contact with the surface to apply the absorbed liquid to the surface. Swab applicators may also be pre-moistened with the desired liquid and sealed in a container for subsequent use. Generally the pre-moistened swab applicators are packaged individually so that opening the packaging to retrieve one swab applicator will not affect the remaining swab applicators.

SUMMARY OF THE INVENTION

The present invention is a multi-fluid applicator with one or more fluids sealed separately within it with opening means enclosed within the applicator to allow the commingling and releasing of the fluids enclosed within the applicator. The enclosed opening means may be operated by bending the applicator at or near the enclosed opening means. Once the enclosed opening means is opened, the fluids sealed within the elongated sealed container will commingle with each other and be released for application or may be released directly for application. There are no loose parts that may be lost and the fluids are completely sealed within the applicator.

DETAILED DESCRIPTION OF THE PREFERRED EMBODIMENT

Figure 1:
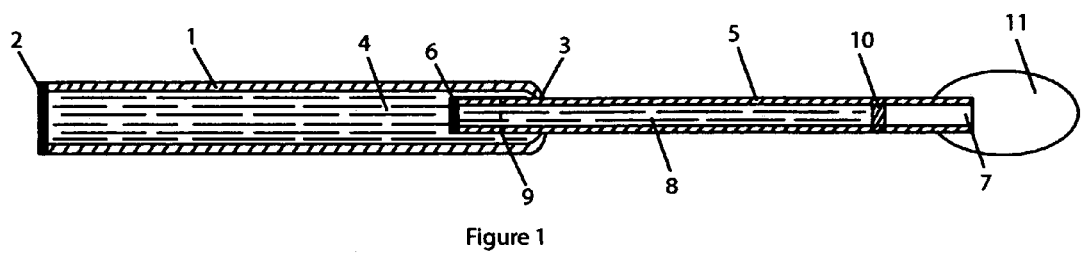
FIG. 1 shows a cross-sectional view of the preferred embodiment of the multi-fluid applicator.

FIG. 1 shows a cross-sectional view of the preferred embodiment of the multi-fluid applicator. In the preferred embodiment, the multi-fluid applicator comprises of a first elongated tubular housing 1 with a sealed end 2 and an open end 3. A first fluid 4 is enclosed within the first elongated tubular housing 1.

A second elongated tubular housing 5 with a sealed end 6 and an open end 7 and with approximately the same outside diameter at a location near its sealed end 6 as the open end 3 of the first elongated tubular housing 1 is inserted with its sealed end 6 inside the open end 3 of the first elongated tubular housing 1 sealing the first fluid 4 within the first elongated tubular housing 1. A second fluid 8 is enclosed within the second elongated tubular housing 5. The second fluid 8 may be the same as or different than the first fluid 4. An opening means 9 in the form of a fracture line is located near the sealed end 6 of the second elongated tubular housing 5 and positioned within the first elongated tubular housing 1 such that the sealed end 6 of the second elongated tubular housing 5 will sever from the remainder of the second elongated tubular housing 5 when the elongated tubular housings 1, 5 are bent near the fracture line to allow the first fluid 4 in the first elongated tubular housing 1 to commingle with the second fluid 8 in the second elongated tubular housing 5.

A viscous substance 10 such as silicone may be disposed near the open end 7 of the second elongated tubular housing 5 to seal the second fluid 8 within the second elongated tubular housing 5 and to prevent evaporation of the second fluid 8. After the opening means 9 is opened, the first fluid 4 will commingle with the second fluid 8 and the two fluids 4, 8 may be ejected from the applicator by squeezing the first elongated tubular housing 1 for application. An applicator tip 11 such as a cotton or foam swab or a brush may be affixed to the open end 7 of the second elongated tubular housing 5 to apply the ejected fluids 4, 8.

The open end 7 of the second elongated tubular housing 5 may also be sealed and provided with a second opening means such as a fracture line to allow complete sealing of the second fluid in the second elongated tubular housing 5. After the opening means 9 is opened, the first fluid 4 will commingle with the second fluid 8 and the two fluids 4, 8 may be ejected from the applicator by opening the second opening means and then squeezing the first elongated tubular housing 1 for application.

The first fluid 4 may also be omitted with the first elongated tubular housing 1 simply filled with a gas, such as air. The fluid sealed in the second elongated tubular housing 5 may be controllably released by first opening the opening means and then squeezing the first elongated tubular housing 1. The rate and amount of the fluid extracted may be controlled by the pressure applied to the first elongated tubular housing 1.

Furthermore, one of the fluids, such as the first fluid 4, may also be replaced with a powder substance wherein when the opening means 9 is opened the fluid in the applicator will mix with the powder substance and subsequently be ejected for application. This is particularly suitable when the application requires that a powder substance be kept dry until application, at which time the dry powder must be mixed with a fluid such as an activating agent.

Figure 2:
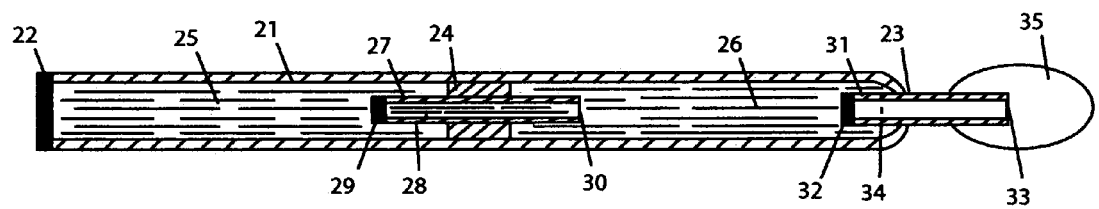
FIG. 2 shows a cross-sectional view of another embodiment of the multi-fluid applicator.

Another embodiment of the multi-fluid applicator is shown in FIG. 2. In this embodiment, the multi-fluid applicator comprises of an elongated tubular housing 21 with a sealed end 22 and an open end 23. A restriction 24 is disposed between the sealed end 22 and the open end 23 generally separating the elongated tubular housing 21 into two sections. A first fluid 25 is enclosed within the first section near the sealed end 22 of the elongated tubular housing 21. A second fluid 26 is enclosed within the second section near the open end 23 of the elongated tubular housing 21. The second fluid 26 may be the same as or different than the first fluid 25.

A first opening means in the form of a first elongated tube 27 with a sealed end 29 and an open end 30 and with approximately the same outside diameter as the restriction 24 of the elongated tubular housing 21 is inserted with its sealed end 29 inside the restriction 24 in the elongated tubular housing 21 sealing the first fluid 25 within the elongated tubular housing 21. A fracture line 28 is located near the sealed end 29 of the first elongated tube 27 such that the sealed end 29 of the first elongated tube 27 will sever from the remainder of the first elongated tube 27 when the elongated tubular housing 21 and the first elongated tube 27 are bent near the fracture line 28.

A second opening means in the form of a second elongated tube 31 with a sealed end 32 and an open end 33 and with approximately the same outside diameter at a location near its sealed end 32 as the open end 23 of the elongated tubular housing 21 is inserted with its sealed end 32 inside the open end 23 of the elongated tubular housing 21 sealing the second fluid 26 within the second section of the elongated tubular housing 21. A fracture line 34 is located near the sealed end 32 of the second elongated tube 31 such that the sealed end 32 of the second elongated tube 31 will sever from the remainder of the second elongated tube 31 when the elongated tubular housing 21 and the second elongated tube 31 are bent near the fracture line 34.

After the first opening means is opened, the first fluid 25 will commingle with the second fluid 26. The second opening means may subsequently be opened to allow extraction of the fluids 25, 26 from the applicator by squeezing the elongated tubular housing 21 for application. An applicator tip 35 such as a cotton or foam swab or a brush may be affixed to the open end 33 of the second elongated tube 31 to apply the extracted fluids 25, 26.

One of the fluids, such as the first fluid 25, may be replaced with a powder substance wherein when the first opening means is opened the fluid in the applicator will mix with the powder substance and subsequently be ejected for application. This is particularly suitable when the application requires that a powder substance be kept dry until application, at which time the dry powder must be mixed with a fluid such as an activating agent.

Figure 3:
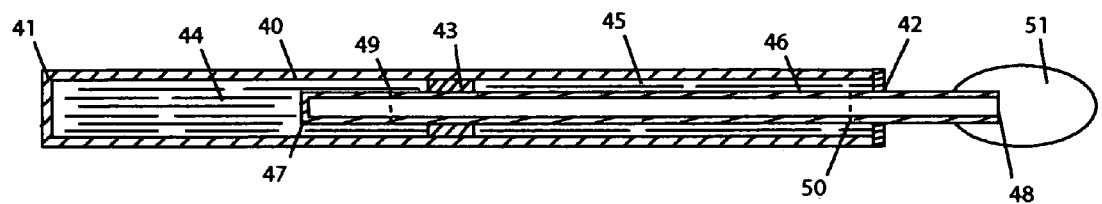
FIG. 3 shows a cross-sectional view of another embodiment of the multi-fluid applicator.

Yet another embodiment of the multi-fluid applicator is shown in FIG. 3. In this embodiment, the multi-fluid applicator comprises of an elongated tubular housing 40 with a sealed end 41 and an open end 42. A restriction 43 is disposed between the sealed end 41 and the open end 42 generally separating the elongated tubular housing 40 into two sections. A first fluid 44 is enclosed within the first section near the sealed end 41 of the elongated tubular housing 40. A second fluid 45 is enclosed within the second section near the open end 42 of the elongated tubular housing 40. The second fluid 45 may be the same as or different than the first fluid 44.

An opening means in the form of an elongated tube 46 with a sealed end 47 and an open end 48 is inserted with its sealed end 47 inside the restriction 43 in the elongated tubular housing 40 sealing the first fluid 44 and the second fluid 45 within the elongated tubular housing 40 and with approximately the same outside diameters located near the restriction 43 and the open end 42 as the restriction 43 and the open end 42 of the elongated tubular housing 40. A first fracture line 49 is located near the sealed end 47 disposed within the first section and a second fracture line 50 is located near the open end 42 of the elongated tubular housing 40 such that the elongated tube 46 will break open when the elongated tubular housing 40 and the elongated tube 46 are bent near the fracture lines 49, 50.

The opening means may be selectively opened to allow the first fluid 44, the second fluid 45, or both fluids 44, 45 to be released from the applicator by squeezing the elongated tubular housing 40 for application. An applicator tip 51 such as a cotton or foam swab or a brush may be affixed to the open end 48 of the elongated tube 46 to apply the extracted fluids 44, 45.

Figure 4:
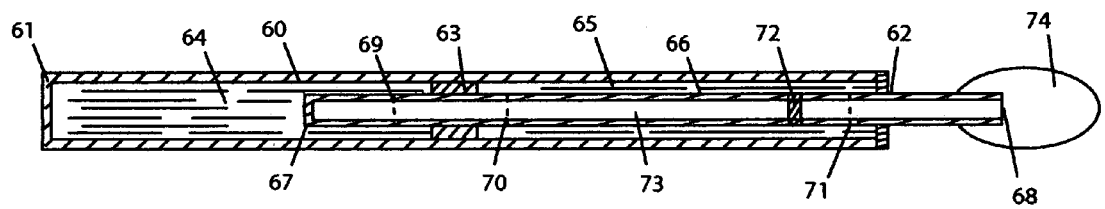
FIG. 4 shows a cross-sectional view of another embodiment of the multi-fluid applicator.

Yet another embodiment of the multi-fluid applicator is shown in FIG. 4. In this embodiment, the multi-fluid applicator comprises of an elongated tubular housing 60 with a sealed end 61 and an open end 62. A restriction 63 is disposed between the sealed end 61 and the open end 62 generally separating the elongated tubular housing 60 into two sections. A first fluid 64 is enclosed within the first section near the sealed end 61 of the elongated tubular housing 60. A second fluid 65 is enclosed within the second section near the open end 62 of the elongated tubular housing 60. The second fluid 65 may be the same as or different than the first fluid 64.

An opening means in the form of an elongated tube 66 with a sealed, end 67 and an open end 68 is inserted with its sealed end 67 inside the restriction 63 in the elongated tubular housing 60 sealing the first fluid 64 and the second fluid 65 within the elongated tubular housing 60 and with approximately the same outside diameters located near the restriction 63 and the open end 62 as the restriction 63 and the open end 62 of the elongated tubular housing 60. A first fracture line 69 is located near the sealed end 61 and positioned such that when the elongated tube 66 is inserted inside the restriction 63 the first fracture line 69 will be inside the first section. A second fracture line 70 is located near the first fracture line 69 opposite the restriction 63. A third fracture line 71 is separated from the first 69 and second 70 fracture lines by a sealed-off section 72 of the elongated tube 66 located near the open end 62 of the elongated tubular housing 60. A third fluid 73 is enclosed by the sealed-off section 72 of the elongated tube 66. The third fluid 73 may be the same as or different than the other two fluids 64, 65. The elongated tube 66 will break open when the elongated tubular housing 60 and the elongated tube 66 are bent near the fracture lines 63, 70, 71.

The opening means may be opened to allow the three fluids 64, 65, 73 to be commingled and released from the applicator by squeezing the elongated tubular housing 60 for application. When the first fracture line 69 is broken, the first fluid 64 will commingle with the third fluid 73. When the second fracture line 70 is broken, the commingled first 64 and third 73 fluids will commingle with the second fluid 65. When the third fracture line 71 is broken, the commingled fluids 64, 65, 73 will be released from the applicator. An applicator tip 74 such as a cotton or foam swab or a brush may be affixed to the open end 68 of the elongated tube 66 to apply the extracted fluids 64, 65, 73.

One of the fluids, such as the first fluid 64, may be replaced with a powder substance wherein when the opening means are opened the fluid in the applicator will mix with the powder substance and subsequently be ejected for application. This is particularly suitable when the application requires that a powder substance be kept dry until application, at which time the dry powder must be mixed with a fluid such as an activating agent.

Figure 5:
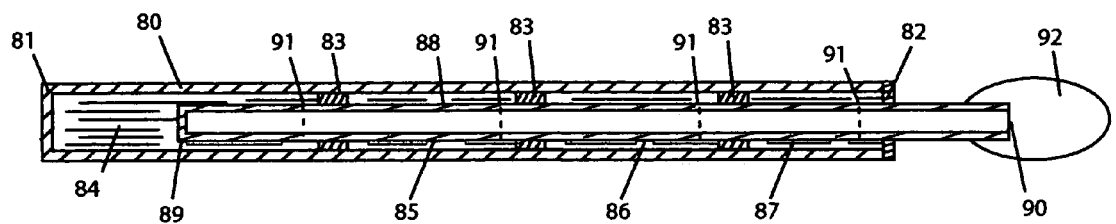
FIG. 5 shows a cross-sectional view of another embodiment of the multi-fluid applicator.

Yet another embodiment of the multi-fluid applicator is shown in FIG. 5. In this embodiment, the multi-fluid applicator comprises of an elongated tubular housing 80 with a sealed end 81 and an open end 82. Multiple restrictions 83 are disposed between the sealed end 81 and the open end 82 generally separating the elongated tubular housing 80 into multiple sections. A fluid 84, 85, 86, 87 is enclosed within each of the sections of the elongated tubular housing 80. The fluids 84, 85, 86, 87 may all be the same fluid or different fluids may be used in each section.

An opening means in the form of an elongated tube 88 with a sealed end 89 and an open end 90 is inserted with its sealed end 89 through all the restrictions 83 in the elongated tubular housing 80 sealing each of the fluids 84, 85, 86, 87 in the respective sections in the elongated tubular housing 80 and with approximately the same outside diameters located near each of the restrictions 83 and the open end 82 as the restrictions 83 and the open end 82 of the elongated tubular housing 80. A fracture line 91 is located near each of the restrictions 83 disposed within each section such that the fluid 84, 85, 86, 87 within a section will be released when the fracture line 91 in that section is broken open when the elongated tubular housing 80 and the elongated tube 88 are bent near the fracture line 91.

The opening means may be selectively opened to allow the desired fluid to be released from the applicator by squeezing the section of the elongated tubular housing 80 with the fluid. An applicator tip 92 such as a cotton or foam swab or a brush may be affixed to the open end 90 of the elongated tube 88 to apply the extracted fluid.

Figure 6:
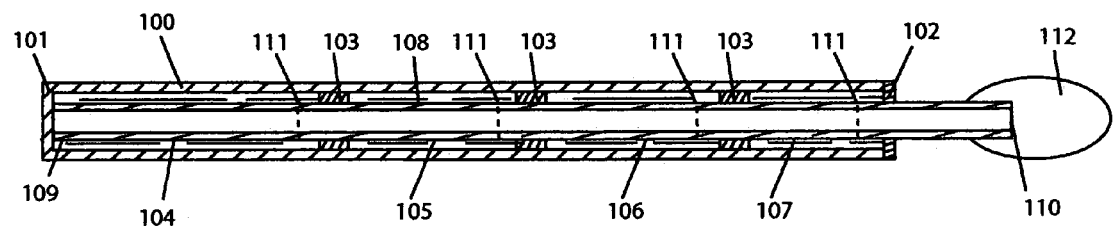
FIG. 6 shows a cross-sectional view of another embodiment of the multi-fluid applicator.

Yet another embodiment of the multi-fluid applicator is shown in FIG. 6. In this embodiment, the multi-fluid applicator comprises of an elongated tubular housing 100 with a sealed end 101 and an open end 102. Multiple restrictions 103 are disposed between the sealed end 101 and the open end 102 generally separating the elongated tubular housing 100 into multiple sections. A fluid 104, 105, 106, 107 is enclosed within each of the sections of the elongated tubular housing 100. The fluids 104, 105, 106, 107 may all be the same fluid or different fluids may be used in each section.

An opening means in the form of an elongated tube 108 with a sealed end 109 affixed to the sealed end 101 of the elongated tubular housing 100 and an open end 110 that extends through all the restrictions 103 in the elongated tubular housing 100 sealing each of the fluids 104, 105, 106, 107 in the respective sections in the elongated tubular housing 100 and with approximately the same outside diameters located near each of the restrictions 103 and the open end 102 as the restrictions 103 and the open end 102 of the elongated tubular housing 100. A fracture line 111 is located near each of the restrictions 103 disposed within each section such that the fluid 104, 105, 106, 107 within a section will be released when the fracture line 111 in that section is broken open when the elongated tubular housing 100 and the elongated tube 108 are bent near the fracture line 111.

The opening means may be selectively opened to allow the desired fluid to be released from the applicator by squeezing the section of the elongated tubular housing 100 with the fluid. An applicator tip 112 such as a cotton or foam swab or a brush may be affixed to the open end 110 of the elongated tube 108 to apply the extracted fluid.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A multi-fluid applicator comprising:
   a first elongated tubular housing with a sealed end and an open end;
   a fluid enclosed within the first elongated tubular housing;
   a second elongated tubular housing with a sealed end and an open end inserted with its sealed end inside the open end of the first elongated tubular housing sealing the fluid within the first elongated tubular housing;
   a liquid enclosed within the second elongated tubular housing; and
   an opening means located near the sealed end of the second elongated tubular housing and positioned within the first elongated tubular housing to allow the fluid in the first elongated tubular housing to commingle with the liquid in the second elongated tubular housing;
   wherein after the opening means is opened, the fluid will commingle with the liquid and the two fluids may be ejected from the applicator by squeezing the first elongated tubular housing for application.

2. A multi-fluid applicator as in claim 1, wherein said opening means is a fracture line near the sealed end of said second elongated tubular housing whereby said sealed end will sever from the remainder of the second elongated tubular housing when the elongated tubular housings are bent near the fracture line.

3. A multi-fluid applicator as in claim 1, wherein a viscous substance is disposed near the open end of the second elongated tubular housing to seal the liquid within the second elongated tubular housing and to prevent evaporation of the liquid.

4. A multi-fluid applicator as in claim 1, wherein an applicator tip is affixed to the open end of the second elongated tubular housing.

5. A multi-fluid applicator as in claim 1, wherein said open end of the second elongated tubular housing is sealed and provided with a second opening means to allow complete sealing of the liquid in the second elongated tubular housing.

6. A multi-fluid applicator as in claim 5, wherein said second opening means is a fracture line near the sealed end of said second elongated tubular housing whereby said sealed end will sever from the remainder of the second elongated tubular housing when the second elongated tubular housing is bent near the fracture line.

7. A multi-fluid applicator as in claims 1, 2, 5, or 6, wherein said fluid is a gas such as air.

8. A multi-fluid applicator as in claim 1, wherein one of the fluids is replaced with a powder substance wherein when the opening means is opened the fluid in the applicator will mix with the powder substance and subsequently be ejected for application.

9. A multi-fluid applicator as in claim 1, wherein said liquid is the same as the first fluid.

10. A multi-fluid applicator comprising:
    an elongated tubular housing with a sealed end and an open end;
    a restriction disposed between the sealed end and the open end generally separating the elongated tubular housing into two sections;
    a first fluid enclosed within the first section near the sealed end of the elongated tubular housing;
    a second fluid enclosed within the second section near the open end of the elongated tubular housing;
    a first opening means disposed at the restriction in the elongated tubular housing sealing the first fluid within the elongated tubular housing; and a second opening means disposed at the open end of the elongated tubular housing sealing the second fluid within the second section of the elongated tubular housing;

wherein after the first opening means is opened, the first fluid will commingle with the second fluid and the second opening means may subsequently be opened to allow extraction of the fluids from the applicator by squeezing the elongated tubular housing for application.

11. A multi-fluid applicator as in claim 10, wherein said first and second opening means are in the form of an elongated tube with a sealed end and an open end and a fracture line near the sealed end of said elongated tube whereby said sealed end will sever from the remainder of the elongated tube when the elongated tubular housing is bent near the fracture line.

12. A multi-fluid applicator as in claim 10, wherein an applicator tip is affixed near the open end of the elongated tubular housing.

13. A multi-fluid applicator as in claim 10, wherein one of the fluids is replaced with a powder substance wherein when the first opening means is opened the fluid in the applicator will mix with the powder substance and subsequently be ejected for application.

14. A multi-fluid applicator as in claim 10, wherein said second fluid is the same as the first fluid.

15. A multi-fluid applicator comprising:
an elongated tubular housing with a sealed end and an open end;
a restriction disposed between the sealed end and the open end generally separating the elongated tubular housing into two sections;
a first fluid enclosed within the first section near the sealed end of the elongated tubular housing;
a second fluid enclosed within the second section near the open end of the elongated tubular housing;
an opening means in the form of an elongated tube with a sealed end and an open end inserted with its sealed end inside the restriction in the elongated tubular housing sealing the first fluid and the second fluid within the elongated tubular housing;
a first fracture line located near the sealed end of the elongated tube disposed within the first section; and
a second fracture line on the elongated tube located near the open end of the elongated tubular housing;
wherein the opening means may be selectively opened to allow the first fluid, the second fluid, or both fluids to be released from the applicator by first bending and then squeezing the elongated tubular housing for application.

16. A multi-fluid applicator as in claim 15, wherein an applicator tip is affixed to the open end of the elongated tube.

17. A multi-fluid applicator as in claim 15, wherein one of the fluids is replaced with a powder substance wherein when both fracture lines of the opening means are fractured the fluid in the applicator will mix with the powder substance and subsequently be ejected for application.

18. A multi-fluid applicator as in claim 15, wherein said second fluid is the same as the first fluid.

19. A multi-fluid applicator comprising:
an elongated tubular housing with a sealed end and an open end;
a restriction disposed between the sealed end and the open end generally separating the elongated tubular housing into two sections;
a first fluid enclosed within the first section near the sealed end of the elongated tubular housing;
a second fluid enclosed within the second section near the open end of the elongated tubular housing;
an opening means in the form of an elongated tube with a sealed end and an open end inserted with its sealed end inside the restriction in the elongated tubular housing sealing the first fluid and the second fluid within the elongated tubular housing;
a first fracture line located near the sealed end of the elongated tube and positioned such that when the elongated tube is inserted inside the restriction the first fracture line will be inside the first section;
a second fracture line located on the elongated tube near the first fracture line opposite the restriction;
a third fracture line on the elongated tube separated from the first and second fracture lines by a sealed-off section of the elongated tube; and
a third fluid enclosed in the elongated tube between the sealed end and the sealed-off section of the elongated tube;
wherein the elongated tube will break open when the elongated tubular housing and the elongated tube are bent near the fracture lines and the opening means may be opened to allow the three fluids to be commingled and released from the applicator by squeezing the elongated tubular housing for application.

20. A multi-fluid applicator as in claim 19, wherein an applicator tip is affixed to the open end of the elongated tube.

21. A multi-fluid applicator as in claim 19, wherein one or more of the fluids is replaced with a powder substance wherein when the fracture lines are broken open the fluid in the applicator will mix with the powder substance and subsequently be ejected for application.

22. A multi-fluid applicator as in claim 19, wherein said second fluid and third fluid are the same as the first fluid.

23. A multi-fluid applicator comprising:
an elongated tubular housing with a sealed end and an open end;
multiple restrictions disposed between the sealed end and the open end generally separating the elongated tubular housing into multiple sections;
a fluid enclosed within one or more of the sections of the elongated tubular housing;
an opening means in the form of an elongated tube with a sealed end and an open end inserted with its sealed end through all the restrictions in the elongated tubular housing sealing the fluids in their respective sections in the elongated tubular housing; and
a fracture line located near each of the restrictions disposed within each section in the elongated tubular housing such that the fluid within a section will be released when the fracture line in that section is broken open when the elongated tubular housing and the elongated tube are bent near the fracture line;
wherein the opening means may be selectively opened to allow the desired fluid to be released from the applicator by squeezing the section of the elongated tubular housing with the fluid.

24. A multi-fluid applicator as in claim 23, wherein an applicator tip is affixed to the open end of the elongated tube.

25. A multi-fluid applicator as in claim 23, wherein one or more of the fluids is replaced with a powder substance wherein when the opening means are opened the fluid in the applicator will mix with the powder substance and subsequently be ejected for application.

26. A multi-fluid applicator as in claim 23, wherein said fluids are all the same.

27. A multi-fluid applicator comprising:
an elongated tubular housing with a sealed end and an open end;
multiple restrictions disposed between the sealed end and the open end generally separating the elongated tubular housing into multiple sections;
a fluid enclosed within one or more of the sections of the elongated tubular housing;
an opening means in the form of an elongated tube with an end affixed to the sealed end of the elongated tubular housing and an open end that extends through all the restrictions in the elongated tubular housing sealing the fluids in their respective sections in the elongated tubular housing; and
a fracture line located near each of the restrictions disposed within each section in the elongated tubular housing such that the fluid within a section will be released when the fracture line in that section is broken open when the elongated tubular housing and the elongated tube are bent near the fracture line;
wherein the opening means may be selectively opened to allow the desired fluid to be released from the applicator by squeezing the section of the elongated tubular housing with the fluid.

28. A multi-fluid applicator as in claim 27, wherein an applicator tip is affixed to the open end of the elongated tube.

29. A multi-fluid applicator as in claim 27, wherein one or more of the fluids is replaced with a powder substance wherein when the opening means are opened the fluid in the applicator will mix with the powder substance and subsequently be ejected for application.

30. A multi-fluid applicator as in claim 27, wherein all the fluids are the same.

* * * * *